US00PP16728P2

(12) United States Plant Patent
Perkins

(10) Patent No.: US PP16,728 P2
(45) Date of Patent: Jun. 27, 2006

(54) ***ANGELONIA* PLANT NAMED 'CARTBAS DEPUR'**

(50) Latin Name: *Angelonia angustifolia*
Varietal Denomination: Cartbas Depur

(75) Inventor: Ralph Tyler Perkins, Gilroy, CA (US)

(73) Assignee: Goldsmith Seeds, INC., Gilroy, CA (US)

( * ) Notice: Subject to any disclaimer, the term of this patent is extended or adjusted under 35 U.S.C. 154(b) by 90 days.

(21) Appl. No.: 11/059,705

(22) Filed: Feb. 17, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent L. Bell
(74) *Attorney, Agent, or Firm*—Jondle & Associates P.C.

(57) ABSTRACT

An *Angelonia* cultivar particularly distinguished by having a purple flower color and a spreading plant habit is disclosed.

1 Drawing Sheet

Figure 1:
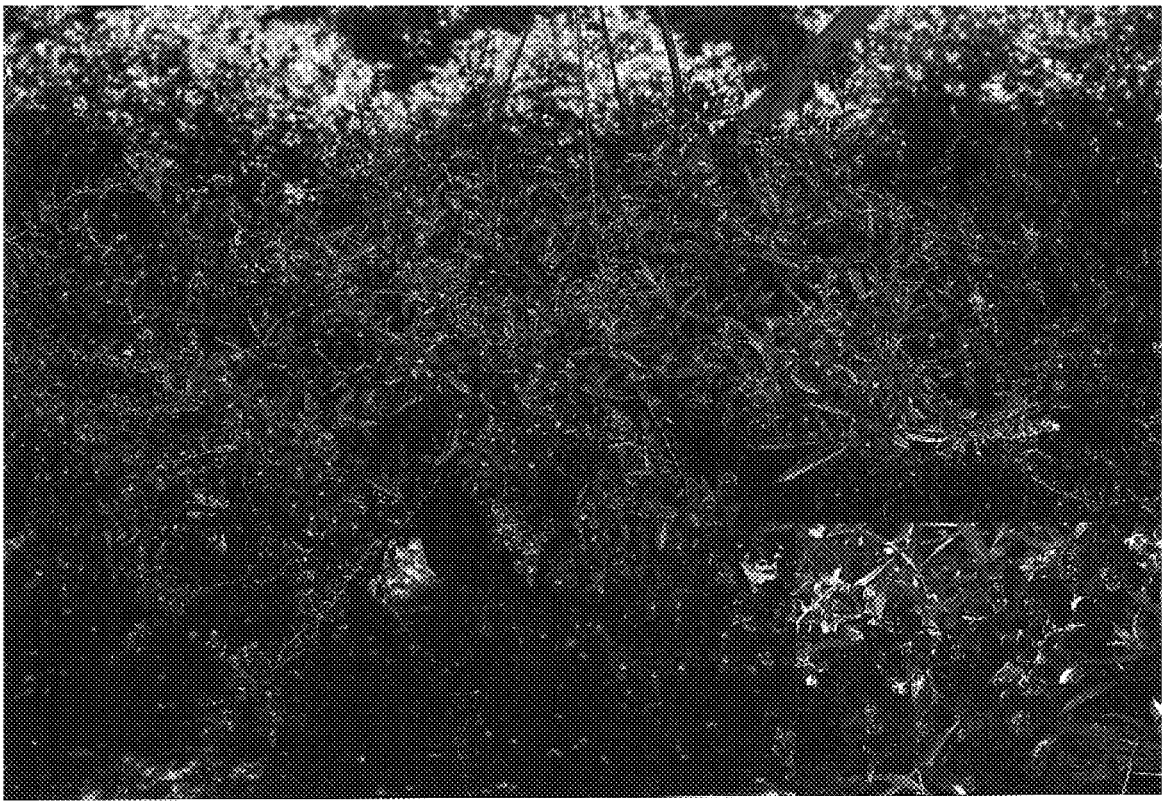

Genus and species: *Angelonia angustifolia.*
Variety denomination: 'Cartbas Depur'.

BACKGROUND OF THE NEW PLANT

The present invention comprises a new and distinct cultivar of *Angelonia*, botanically known as *Angelonia angustifolia*, and hereinafter referred to by the cultivar name 'Cartbas Depur'. The new cultivar originated from a cross between the *Angelonia* cultivar 'Cartbas Depink' (U.S. Plant patent application Ser. No. 11/059,707), which has a deep pink flower color, and the unpatented proprietary *Angelonia* line 60-1, which has purple and white flowers.

The new cultivar was created and selected as a single plant within the progeny of the stated cross in 2001 in Gilroy, Calif. and has been asexually reproduced repeatedly in a controlled environment by vegetative cuttings and tissue culture in Gilroy, Calif. and Andijk, The Netherlands over a two-year period. The plant has also been trialed at Gilroy, Calif., Litchfield, Mich. and Andijk, The Netherlands. 'Cartbas Depur' has been shown to reproduce true to type in successive generations of asexual propagation.

DESCRIPTION OF THE PHOTOGRAPH

This new *Angelonia* plant is illustrated by the accompanying photograph which shows the plant's form, foliage and flowers. The colors shown are as true as can be reasonably obtained by conventional photographic procedures.

FIG. 1. shows the mature plant's form, foliage and flowers. The inset shows a closer view of the flowers.

DESCRIPTION OF THE NEW CULTIVAR

The following detailed description sets forth the distinctive characteristics of 'Cartbas Depur'. The data which define these characteristics were collected from asexual reproductions carried out in Gilroy, Calif. The detailed description was taken on 3–4 month old plants grown in one-gallon containers in a poly-covered greenhouse. Color readings were taken in the late Summer season under natural light. Color references are primarily to The R.H.S. Colour Chart of The Royal Horticultural Society of London (R.H.S.), 2001 edition.

DETAILED BOTANICAL DESCRIPTION

Classification:
- *Family.*—Scrophulariaceae.
- *Bontanical.*—*Angelonia angustifolia.*
- *Common.*—Angel flower.

Parentage:
- *Male parent.*—Proprietary line 60-1 (unpatented).
- *Female parent.*—'Cartbas Depink' (U.S. Plant patent application Ser. No. 11/059,707.

Plant description:
- *Form.*—Prostrate and outwardly spreading.
- *Habit.*—Vigorous habit, well-branched; pinching 1–2 times after transplanting enhances branching.
- *Height.*—10–15 cm, as measured from the base of the plant.
- *Width.*—50–55 cm, as measured from the widest portion of the plant.

Propagation:
- *Time to initiate and develop roots.*—18–23 days.
- *Root description.*—Fibrous, free branching.
- *Time to produce a finished flowering plant.*—8–10 weeks for a 4–6 inch pot.
- *Outdoor plant performance.*—Does well in full sun; free-flowering through the summer; some heat tolerance. Used in mixed container plantings and hanging baskets.

Stems:
- *Length.*—35–40 cm, as measured from the base of the plant.
- *Diameter.*—0.3 cm as measured at the midpoint of the stem.
- *Internode length.*—3.6–3.8 cm.
- *Color.*—RHS 143B.
- *Texture.*—Many glandular hairs of various sizes.
- *Stem anthocyanin.*—Weak and brownish.

Leaves:
- *Arrangement.*—Opposite.
- *Mature leaves.*—Length, fully expanded: 8.5–9.3 cm. Width: 1.3–1.5 cm. Shape: Linear, slightly elliptic.

Margin: Serrate. Apex: Acute. Base: Cuneate. Color: Upper surface: RHS 137A. Lower surface: RHS 137B. Texture: Glandular hairs of various sizes. Venation: Pinnate. Venation color: RHS 137A in the leaf (lower surface); RHS 144B midvein (Entire lower surface and towards base on upper surface).

Flower bud:

*Shape.*—Orbicular.

*Diameter.*—0.5–0.7 cm.

*Length.*—0.7–0.9 cm.

*Color at tight bud.*—RHS 143C with a spot of RHS 187B.

Inflorescence:

*Blooming habit.*—Continuous throughout the growing season; good floriferousness.

*Lastingness of individual blooms.*—6–9 days.

*Fragrance.*—None.

*Inflorescence type.*—Terminal raceme.

*Floret type.*—Single flowers; mostly two in a leaf axis; 5 petals fused at the base.

*Florets per raceme.*—48–56.

*Floret depth.*—0.7 cm.

*Floret (limb) diameter.*—2.0–2.2 cm.

Flower description:

*Flower color.*—Upper surface: Closest to RHS 87A but a little darker. Lower surface: RHS 87A.

*Corolla color inside.*—RHS 155C but whiter, with RHS 86A spots.

*Petals.*—Size: Uppper lip: Length: 0.6 cm from the corolla opening. Width: 0.9 cm. Lower lip, lateral petal: Length: 0.8 cm from the corolla opening. Width: 0.9 cm. Lower lip, mid-petal: Length: 0.8 cm from the corolla opening. Width: 0.9 cm. Apex: Rounded. Base: Fused. Margin: Entire. Texture: Papillose.

*Sepals.*—Sepal number: 5, fused. Color (Upper surface): RHS 141A. Length: 0.4–0.5 cm. Width: 0.2 cm. Shape: Lanceolate. Apex: Acute. Margin: Entire. Anthocyanin: Brown, deepest at base fading to none at apex. Texture: Many short glandular hairs.

*Pedicels.*—Color: RHS 186C with undertones of RHS 143A. Length: 2.0 cm. Diameter: 0.1 cm. Texture: Many glandular hairs of various sizes.

Reproductive organs:

*Stamens.*—4, in pairs.

*Filament color.*—RHS 155C but whiter.

*Filament length.*—0.35 cm.

*Anther color.*—RHS 187B.

*Pollen amount.*—Scarce.

*Pistil.*—One.

*Pistil length.*—0.30–0.35 cm.

*Stigma color.*—RHS 155C but whiter.

*Style color.*—RHS 155C but whiter.

Disease and insect resistance: Not observed.

COMPARISON WITH PARENTAL LINES AND KNOWN CULTIVARS

'Cartbas Depur' differs from the female parent, 'Cartbas Depink' (U.S. Plant patent application Ser. No. 11/059,707), in that 'Cartbas Depur' has a purple flower color while 'Cartbas Depink' has a deep pink flower color. 'Cartbas Depur' differs from the male parent, proprietary line 60-1 (unpatented), in that 'Cartbas Depur' has a purple flower color while 60-1 has a purple and white flower color.

'Cartbas Depur' is most similar to the commercial cultivar 'Balangbeke' (U.S. Plant Pat. No. 15,546), however, there are differences. 'Cartbas Depur' has a more compact habit, darker foliage color, larger flower size and brighter purple flower color than 'Angelmist Basket Deep Purple'.

I claim:

1. A new and distinct *Angelonia* plant as shown and described herein.

* * * * *